United States Patent
Hofmeister et al.

[11] Patent Number: 5,972,915
[45] Date of Patent: Oct. 26, 1999

[54] PESTICIDE CONTAINING A SYNERGISTIC COMBINATION OF ACTIVE INGREDIENTS

[75] Inventors: Peter Hofmeister, Neustadt; Ulrich Neumann, Schifferstadt; Volker Harries, Frankenthal; Jürgen von der Heyde, Zwingenberg; Manfred Schroeder, Neustadt; Jörn Tidow, Schwetzingen; Matthias Bratz; Karl-Friedrich Jäger, both of Limburgerhof, all of Germany

[73] Assignee: BASF Aktiengesellschaft, Ludwigshafen, Germany

[21] Appl. No.: 08/930,169

[22] PCT Filed: Apr. 4, 1996

[86] PCT No.: PCT/EP96/01513

§ 371 Date: Oct. 9, 1997

§ 102(e) Date: Oct. 9, 1997

[87] PCT Pub. No.: WO96/33613

PCT Pub. Date: Oct. 31, 1996

[30] Foreign Application Priority Data

Apr. 22, 1995 [DE] Germany .......................... 195 14 903

[51] Int. Cl.⁶ .......................... A01N 57/00; A01N 57/10; A61K 31/54
[52] U.S. Cl. .............................. 514/119; 514/92; 514/94; 514/144; 514/223.8
[58] Field of Search ................................ 514/223.8, 119, 514/92, 94, 144

[56] References Cited

U.S. PATENT DOCUMENTS

| | | | |
|---|---|---|---|
| 2,838,389 | 6/1958 | Yoder | 71/215 |
| 3,265,561 | 8/1966 | Werres et al. | 167/22 |
| 4,855,140 | 8/1989 | Seppelt et al. | 424/405 |

FOREIGN PATENT DOCUMENTS

233 780  3/1986  Germany .

OTHER PUBLICATIONS

Worthing et al, The Pesticides Manual, 9th Ed. pp. 225–226 (1991).
Agronomia Columbiana, 1991, vol. 8, No. 2, 248–252.
Derwent Abst. JP 48 038 139 (1973).
Derwent Abst. JP 58 170 706 (1983).

*Primary Examiner*—Allen J. Robinson
*Attorney, Agent, or Firm*—Keil & Weinkauf

[57] ABSTRACT

A pesticide comprising an active ingredient combination consisting of
a) tetrahydro-3,5-dimethyl-1,3,5-thiadiazine-2-thione of the formula

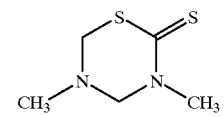

(I)

and
b) O-(O-ethyl-S-n-propylphosphoryl)-O-(N-methylcarbamoyl)pyrocatechol of the formula

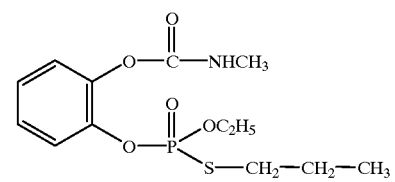

(II)

and/or
c) O-ethyl S,S-dipropyl phosphorodithioate of the formula

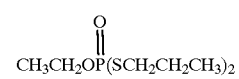

(III)

and/or
d) 2-methyl-2-methylthiopropionaldehyde O-methylcarbamoyloxime of the formula

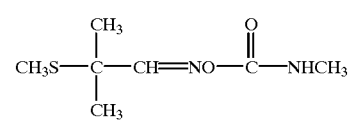

(IV)

and/or
e) N,N-dimethyl-2-methylcarbamoyloximino-2-methylthioacetamide of the formula

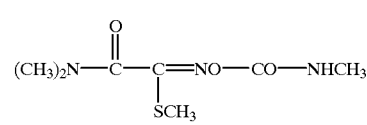

(V)

and/or
f) ethyl-4-methylthio-m-tolylisopropylphosphoramide of the formula

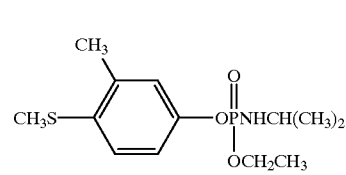

(VI)

and/or g) (RS)-S-sec-butyl O-ethyl 2-oxo-1,3-thiazolidin-3-ylphosphono-thioate of the formula

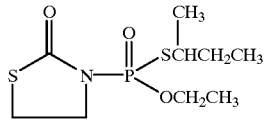
(VII)

and/or h) 2,3-dihydro-2,2-dimethylbenzofuran-7-yl methylcarbamate of the formula

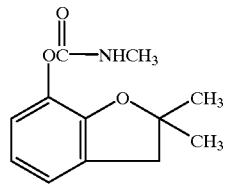
(VIII)

and/or i) S-tert-butylthiomethyl O,O-diethyl phosphorodithioate of the formula

(IX)

and/or j) S,S-di-sec-butyl O-ethyl phosphorodithioate of the formula

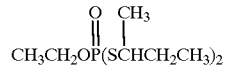
(X)

and/or k) (RS)-O-1-(4-chlorophenyl)pyrazol-4-yl O-ethyl S-propyl phosphorothioate of the formula

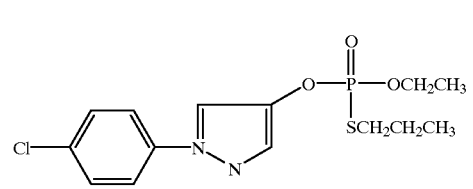
(XI)

and its use as a pesticide are described.

14 Claims, No Drawings

PESTICIDE CONTAINING A SYNERGISTIC COMBINATION OF ACTIVE INGREDIENTS

This application is a 371 of PCT/EP96/01513, filed Apr. 4, 1996.

The present invention relates to a pesticide which comprises an active ingredient combination consisting of a) tetrahydro-3,5-dimethyl-1,3,5-thiadiazine-2-thione of the formula

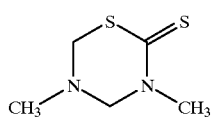

(I)

and b) O-(O-ethyl-S-n-propylphosphoryl)-O-(N-methylcarbamoyl)pyrocatechol of the formula

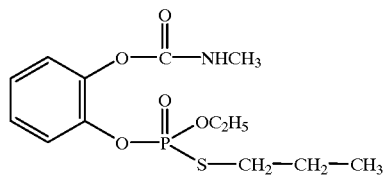

(II)

and/or c) O-ethyl S,S-dipropyl phosphorodithioate of the formula

(III)

and/or d) 2-methyl-2-methylthiopropionaldehyde O-methylcarbamoyloxime of the formula

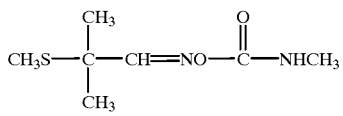

(IV)

and/or e) N,N-dimethyl-2-methylcarbamoyloximino-2-methylthioacetamide of the formula

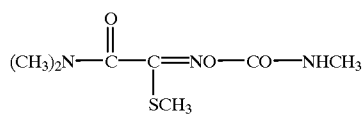

(V)

and/or f) ethyl-4-methylthio-m-tolylisopropylphosphoramide of the formula

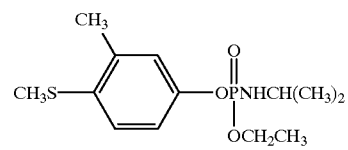

(VI)

and/or g) (RS)-S-sec-butyl O-ethyl 2-oxo-1,3-thiazolidin-3-ylphosphonothioate of the formula

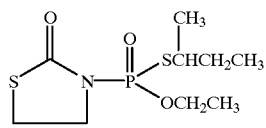

(VII)

and/or h) 2,3-dihydro-2,2-dimethylbenzofuran-7-yl methylcarbamate of the formula

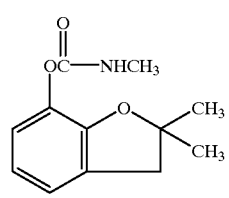

(VIII)

and/or i) S-tert-butylthiomethyl O,O-diethyl phosphorodithioate of the formula

(IX)

and/or j) S,S-di-sec-butyl O-ethyl phosphorodithioate of the formula

(X)

and/or k) (RS)-O-1-(4-chlorophenyl)pyrazol-4-yl O-ethyl S-propyl phosphorothioate of the formula

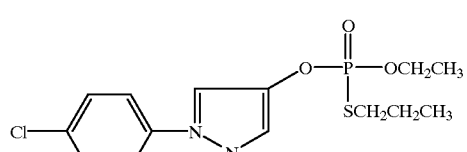

(XI)

in a synergistically active amount.

The invention additionally relates to methods of controlling pests and to the use of the compound I and one or more of the compounds II to XI for preparing pesticides of this type.

The compound of the formula I (common name dazomet), its preparation and its action against pests are disclosed in the literature (U.S. Pat. No. 2,838,389; WO 93/13085). The compounds of the formulae II to XI, their preparation and their action against pests are also disclosed:

Compound II (EP-B-0309843);

Compound III, common name ethoprophos, (U.S. Pat. Nos. 3,112,244; 3,268,393);

Compound IV, common name aldicarb, (U.S. Pat. No. 3,217,037);

Compound V, common name oxamyl, (U.S. Pat. Nos. 3,530,220; 3,658,870);

Compound VI, common name fenamiphos, (DE 1 121 882); U.S. Pat. No. 2,978,479);

Compound VII, common name fosthiazate, (The Pesticide Manual, 9th Edition, No. 6805);

Compound VIII, common name carbofuran, (DE 1 493 646; U.S. Pat. Nos. 3,474,170; 3,474,171);

Compound IX, common name terbufos, (The Pesticide Manual, 9th Edition, No. 11300);

Compound X, common name cadusafos, (The Pesticide Manual, 9th Edition, No. 1835);

Compound XI, common name pyraclofos, (The Pesticide Manual, 9th Edition, No. 10 335).

With respect to lowering application rates and improving the spectrum of action of the known compounds, the object of the present invention was based on mixtures which, together with a decreased total amount of applied active ingredients, have an improved action against pests (synergistic mixtures).

The compositions defined at the outset were accordingly found. It was additionally found that pests can be better controlled with simultaneous joint or separate application of the compound I and one or more of the compounds II to XI or with application of the compound I and one or more of the compounds II to XI in succession than with the individual compounds.

The pesticides according to the invention are suitable for effectively controlling pests of the insects, arachnids and nematodes classes. They are moreover suitable for effectively controlling harmful soil fungi and phytotoxic soil bacteria, eg. *Agrobacterium tumefaciens*, and germinating plants. They can be employed as pesticides in crop protection and in the hygiene and stored materials protection sector. They are advantageously used as soil disinfectants.

The harmful insects include from the order of the butterflies (Lepidoptera), for example, *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholita funebrana, Grapholita molesta, Heliothis armigera, Heliothis virescens, Heliothis zea, Hellula undalis, Hibernia defoliaria, Hyphantria cunea, Hyponomeuta malinellus, Keifferia lycopersicella, Lambdina fiscellaria, Laphygma exigua, Leucoptera coffeella, Leucoptera scitella, Lithocolletis blancardella, Lobesia botrana, Loxostege scitella, Lithocolletis blancardella, Lobesia botrana, Loxostege sticticalis, Lymantria dispar, Lymantria monacha, Lyonetia clerkella Malacosoma neustria, Mamestra brassicae, Orgyia pseudotsugata, Ostrinia nubilalis, Panolis flamea, Pectinophora gossypiella, Peridroma saucia, Phalera bucephala, Phthorimaea operculella, Phyllocnistis citrella, Pieris brassicae, Plathypena scarbra, Plutella xylostella, Pseudoplusia includens, Phyacionia frustrana, Scrobipalpula absoluta, Sitotroga cerelella, Sparganothis pilleriana, Spodoptera frugiperda, Spodoptera littoralis, Spodoptera litura, Thaumatopoea pityocampa, Tortrix viridana, Trichoplusia ni, Zeiraphera canadensis.*

From the order of the beetles (Coleoptera), for example, *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Onlema oryzae, Ortiorrhynchus sulcatus, Ortiorrhynchus ovatus, Phaedon cochlearia, Phyllotreta chrysocephala, Phyllophaga sp., Phyllopertha horticola, Phyllotreta nemorum, Phyllotreta striolata, Popillia japonica, Sitona lineatus, Sitophilus granaria.*

From the order of the dipterous insects (Diptera), for example, *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossia morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea, Tipula paludosa.*

From the order of the thrips (Thysanoptera), for example, *Frankliniella fusca, Frankliniella occidentalis, Frankliniella tritici, Scirtothrips citri, Thrips oryzae, Thrips palmi, Thrips tabaci.*

From the order of the hymenopterous insects (Hymenoptera), for example, *Athalia rosae, Atta cephalotes, Atta sexdens, Atta texana, Hoplocampa minuta, Hoplocampa testudinea, Momomorium pharaonis, Solenopsis geminata, Solenopsis invicta.*

From the order of the bugs (Heteroptera), for example, *Acrosternum hilare, Blissus leucopterus, Cyrtopeltis notatus, Dysdercus cingulatus, Dysdercus intermedius, Eurygaster integriceps, Euchistus impictiventris, Leptoglossus phyllopus, Lygus lineolaris, Lygus pratensis, Nezara, yiridula, Piesma quadrata, Solubea insularis, Thyanta perditor.*

From the order of the plant-sucking insects (Homoptera), for example, *Perkinsiella saccaricida* (sugar cane leafhopper), *Nilaparvata lugens* (brown planthopper),

*Empoasca fabae* (potato leafhopper), *Psylla mali* (apple leaf sucker), *Psylla piri* (pear-tree psylla), *Trialeurodes vaporariorum* (glasshouse whitefly), *Aphis fabae* (black bean aphid), *Aphis pomi* (green apple aphid), *Aphis sambuci* (elder aphid), *Aphidula nasturtii* (buckthorn aphid), *Cerosipha gossypii* (melon aphid), *Sappaphis mali* (rosy apple aphid), *Sappaphis mala* (pear aphid), *Dysaphis radicola*, *Brachycaudus cardui* (thistle aphid), *Brevicoryne brassicae* (cabbage aphid), *Phorodon humuli* (hop aphid), *Rhopalomyzus ascalonicus* (shallot aphid), *Myzodes persicae* (green peach aphid), *Myzus cerasi* (black cherry aphid), *Dysaulacorthum pseudosolani* (green potato aphid), *Acyrthosiphon onobrychis* (green pea louse), *Macrosiphon rosae* (rose aphid), *Megoura viciae* (vetch aphid), *Schizoneura lanuginosa* (woolly pear aphid), *Pemphigus bursarius* (lettuce root aphid), *Dreyfusia nordmannianae* (silver fir migratory adelges), *Dreyfusia piceae* (balsam wooly aphid), *Adelges laricis* (larch adelges), *Viteus vitifolii* (vine louse); from the order of the termites (Isoptera), for example, *Reticulitermes lucifugus, Calotermes flavicollis, Leucotermes flavipes, Termes natalensis*.

From the order of the orthopterous insects (Orthoptera), for example, *Forficula auricularia, Acheta domestica, Gryllotalpa gryllotalpa, tachycines asynamorus, Locusta migratoria, Stauronotus meroccanus, Schistocerca peregrina, Nomadacris septemfasciata, Melanoplus spretus, Melanoplus femur-rubrum, Blatta orientalis, Blattella germanica, Periplaneta americana, Blabera gigantes*.

The Arachnoidea class includes arachnids (Acarina), for example, *Ixodes ficinus, Ornithodorus moubata, Amblyomma americanum, Dermacentor silvarum, Boophilus microplus, Tetranychus telarius, Tetranychus pacificus, Paratetranychus pilosus, Bryobia praetiosa*.

The nematodes class includes, for example, root gall nematodes, eg. *Meloidogyne hapla, Meloidogyne incognita, Meloidogyne javenica*, cyst-forming nematodes, eg. *Globodera rostochiensis, Heterodera avenae, Heterodera glycinae, Heterodera schachtii, Heterodera trifolii*, stem and leaf eelworms, eg. *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchlorhynchus claytoni, Tylenchorhynchus dubius, Paratylenchus neglectus, Paratylenchus penetrans, Paratylenchus curvitatus, Paratylenchus goodeyi*.

The harmful fungi include Fusarium, Pythium, Rhizoctonia, Sclerotinia, Verticillium spp., Colletotrichum coccodes.

In general, the pesticides according to the invention contain from 0.1 to 99% by weight, preferably from 0.1 to 98% by weight, in particular from 0.1 to 95% by weight, of the active ingredient combination.

In the pesticides according to the invention, the weight ratio of the compound of the formula I to one or more of the compounds of the formulae II to XI is in general from 1,000:1 to 0.1:1, preferably from 500:1 to 1:1, in particular from 500:1 to 10:1.

The application rate of the active ingredient combination under outdoor conditions is in general from 0.1 to 1,000 kg/ha, preferably from 0.5 to 500 kg/ha, in particular from 1 kg to 300 kg/ha.

The pesticides according to the invention are preferably employed for controlling soil pests such as nematodes, harmful soil fungi, soil insects, phytotoxic soil bacteria and germinating plants, and they are particularly advantageously used for controlling nematodes. This is expediently carried out by employing the pesticides as soil disinfectants, eg. by applying the pesticides as uniformly as possible to the soil surface of the soil to be treated in suitable form, for example in the form of granules. The composition applied is then incorporated into the soil, expediently to a depth of from 5 to 40 cm, preferably from 10 to 30 cm. The period of soil disinfection until new sowing depends greatly on the soil temperature and can be from 5 to 45 days, eg. in the range from 12 to 20 days at soil temperatures of from 12 to 18° C.

The active compounds can be applied as such, in the form of their formulations or in the application forms prepared therefrom, eg. in the form of powders, suspensions or dispersions, emulsions, pastes, broadcasting compositions and granules. The application forms depend wholly on the intended uses. As a rule, the pesticides according to the invention are applied in the form of granules.

The following examples illustrate the invention.

Formulation examples for the preparation of mixed granule formulations

FORMULATION EXAMPLE 1

96 parts by weight of tetrahydro-3,5-dimethyl-1,3,5-thiadiazine-2-thione (I) are initially introduced into a Nauta mixer and heated to 60° C. 1.5 parts by weight of O-(O-ethyl-S-n-propylphosphoryl) O-(N-methylcarbamoyl) pyrocatechol (II) are melted and sprayed onto the particle surfaces of the initially introduced active ingredient I at 65° C. in the running mixer. After spraying-on has been completed, 0.5 parts by weight of a finely powdered calcium silicate are uniformly added to the mixture. Combination granules having good flow properties are obtained.

FORMULATION EXAMPLE 2

96 parts by weight of tetrahydro-3,5-dimethyl-1,3,5-thiadiazine-2-thione (I) are initially introduced into a Lödige intensive mixer and mixed at room temperature. 1.5 parts by weight of N,N-dimethyl-2-methylcarbamoyloximino-2-methylthioacetamide (V) are added and the mixture is simultaneously sprayed with 3 parts by weight of an aqueous, 10% strength by weight polyvinyl alcohol solution.

After the addition and spraying-on phase has been completed, the moist granules are dried in a fluidized bed dryer at 60° C. Combination granules having good flow properties result.

USE EXAMPLES

In the following examples, the pesticides according to the invention were investigated with respect to their action on root gall nematodes of the genus Meloidogyne on potted tomatoes in a greenhouse.

In Examples 1–3, mixtures according to the invention of tetrahydro-3,5-dimethyl-1,3,5-thiadiazine-2-thione (dazomet) (I) and O-(O-ethyl-S-n-propylphosphoryl)-O-(N-methylcarbamoyl)pyrocatechol (II) were investigated, which were compared with the action of the individual compounds I, II and VII (fosthiazate) and also the soil disinfection agents dichloropropene/dichloropropane (D—D), which were tested in the comparison tests V1 to V5, and with the untreated tomato plants.

I was employed here as granules containing 98% by weight of active ingredient, II as a formulation containing 4.2% by weight of active ingredient, VII as a formulation containing 1% by weight of active ingredient and D—D 92% strength by weight in an oily formulation.

Assessment was carried out 74 days after planting the tomato plants.

| Ex. | Active ingredient | Application rate (kg/a.i./ha) | Intensity of the action of the nematodes on the tomato plants (%) | Height of the plants (cm) |
|---|---|---|---|---|
| 1 | I (98% strength) | 196.0 | 0.0 | 120.0 |
|   | II (4.2% strength) | +3.0 |  |  |
| 2 | I (98% strength) | 196.0 | 0.0 | 119.0 |
|   | II (4.2% strength) | 1.5 |  |  |
| 3 | I (98% strength) | 98.0 | 0.0 | 115.2 |
|   | II (4.2% strength) | 3.0 |  |  |
| V1 | II (4.2% strength) | 6.0 | 50.0 | 104.2 |
| V2 | I (98% strength) | 196.0 | 3.3 | 111.0 |
| V3 | I (98% strength) | 98.0 | 10.0 | 112.5 |
| V4 | VII (1% strength) | 3.0 | 23.3 | 108.0 |
| V5 | D-D (92% strength) | 138.0 | 0.0 | 98.5 |
| untreated |  |  | 100.0 | 80.2 |

We claim:
1. A pesticidal composition, comprising
a) tetrahydro-3,5-dimethyl-1,3,5-thiadiazine-2-thione of the formula I

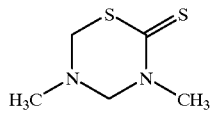
(I)

and at least one further active ingredient selected from the group consisting of
b) O-(O-ethyl-S-n-propylphosphoryl)-O-(N-methylcarbamoyl)-pyrocatechol of the formula II (II)

c) O-ethyl S,S-dipropyl phosphorodithioate of the formula III (III)

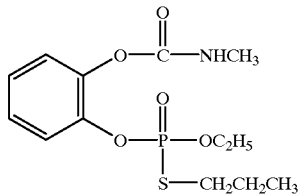

d) (RS)-S-sec-butyl O-ethyl 2-oxo-1,3-thiazolidin-3-yl-phosphonothioate of the formula VII (VII)

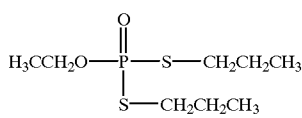

e) S-tert-butylthiomethyl O,O-diethyl phosphorodithioate of the formula IX (IX)

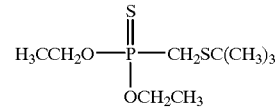

f) S,S-di-sec-butyl O-ethyl phosphorodithioate of the formula X (X)

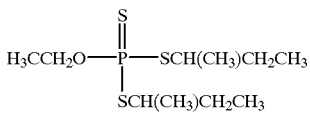

and
g) (RS)-O-1-(4-chlorophenyl)pyrazol-4-yl O-ethyl S-propyl phosphorothioate of the formula XI (XI)

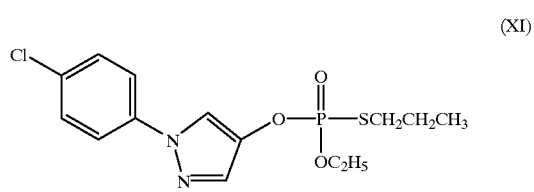

in a synergistically active amount.
2. The composition defined in claim 1, further comprising customary carriers.
3. The composition defined in claim 1, wherein the further active ingredient is O-(O-ethyl-S-n-propylphosphoryl)-O-(N-methylcarbamoyl)-pyrocatechol of the formula II.
4. The composition defined in claim 3, further comprising customary carriers.
5. The composition defined in claim 4, which contains from 0.1 to 99% by weight of the thiadiazine-2-thione of the formula I and the further active ingredient.
6. The composition defined in claim 3, wherein the weight ratio of the thiadiazine-2-thione of the formula I to the further active ingredient is from 1,000:1 to 0.1:1.
7. The composition defined in claim 2, which contains from 0.1 to 99% by weight of the thiadiazine-2-thione of the formula I and the further active ingredient.
8. The composition defined in claim 1, wherein the weight ratio of the thiadiazine-2-thione of the formula I to the further active ingredient is from 1,000:1 to 0.1:1.

9. A method of controlling pests, which comprises treating the pests or the areas or spaces to be kept free from pests with a pest-active, synergistically effective amount of the thiadiazine-2-thione of the formula I as defined in claim 1 and the further active ingredient as defined in claim 1.

10. A method of soil disinfection, which comprises treating the soil with an active, synergistically effective amount of the thiadiazine-2-thione of the formula I as defined in claim 1 and the further active ingredient as defined in claim 1.

11. A method of controlling nematodes, harmful soil fungi and soil insects, which comprises treating the ground with an active, synergistically effective amount of the thiadiazine-2-thione of the formula I as defined in claim 1 and the further active ingredient as defined in claim 1.

12. The method of claim 9, wherein the further active ingredient is O-(O-ethyl-S-n-propylphosphoryl)-O-(N-methylcarbamoyl)-pyrocatechol of the formula II.

13. The method of claim 10, wherein the further active ingredient is O-(O-ethyl-S-n-propylphosphoryl)-O-(N-methylcarbamoyl)-pyrocatechol of the formula II.

14. The method of claim 11, wherein the further active ingredient is O-(O-ethyl-S-n-propylphosphoryl)-O-(N-methylcarbamoyl)-pyrocatechol of the formula II.

\* \* \* \* \*

UNITED STATES PATENT AND TRADEMARK OFFICE
CERTIFICATE OF CORRECTION

PATENT NO.: 5,972,915

DATED: October 26, 1999

INVENTOR(S): HOFMEISTER et al.

It is certified that error appears in the above-identified patent and that said Letters Patent is hereby corrected as shown below:

On the title page

Item [22] on the cover sheet, "Apr. 4, 1996" should be --Apr. 9, 1996--.

Signed and Sealed this

Second Day of May, 2000

Attest:

Q. TODD DICKINSON

Attesting Officer

Director of Patents and Trademarks